United States Patent [19]
Morrison

[11] 4,039,941
[45] Aug. 2, 1977

[54] GAS SENSOR

[75] Inventor: Stanley R. Morrison, Los Altos, Calif.

[73] Assignee: Stanford Research Institute, Menlo Park, Calif.

[21] Appl. No.: 575,949

[22] Filed: May 9, 1975

[51] Int. Cl.² .................................. G01N 27/00
[52] U.S. Cl. ........................ 324/71 SN; 340/237 S; 23/254 E; 23/232 E; 338/34
[58] Field of Search ............ 324/71 SN, 65 R; 340/237 S; 338/34, 13; 357/25; 73/26, 27 R; 23/254 E, 232 E

[56] References Cited
U.S. PATENT DOCUMENTS

| | | | |
|---|---|---|---|
| 3,625,756 | 12/1971 | Taguchi | 117/201 |
| 3,676,820 | 7/1972 | Taguchi | 338/34 |
| 3,695,848 | 10/1972 | Taguchi | 23/254 E |
| 3,865,550 | 2/1975 | Bott et al. | 23/232 E |
| 3,901,067 | 8/1975 | Boardman, Jr. et al. | 73/23 |

Primary Examiner—Rudolph V. Rolinec
Assistant Examiner—Vincent J. Sunderdick
Attorney, Agent, or Firm—Lindenberg, Freilich

[57] ABSTRACT

A gas sensor is provided here comprising a semi-conductor support coated with a material which reacts with a specific gas as a result of which it exchanges electrons with the support. By measuring the resulting change in conductivity of the support, one can detect the presence of the particular gas as well as its concentration.

6 Claims, 3 Drawing Figures

4,039,941

GAS SENSOR

ORIGIN OF THE INVENTION

The invention described herein was made in the course of work under a contract from the U.S. Army Research Office.

BACKGROUND OF THE INVENTION

This invention relates to gas detectors and more particularly to improvements in solid state gas detectors.

Gas detecting apparatus exists which uses semiconductor material as a gas detector. Usually the apparatus operates on the basis of a direct semiconductor gas interaction. A measurement of the conductivity or resistivity of the semiconductor is taken as a indication of the presence and/or quantity of the particular gas for which the semiconductor is sensitive. Another technique is to detect a change in the rectifying or conducting properties of semiconductor diodes when exposed to gases. There are two basic problems with these prior art systems. One of these is that for the case of direct semiconductor/gas interaction, chemical interactions leading to the electrical response of the semiconductor are not usually reversible so that the signal output for a given gas pressure depends on the previous history of the semiconductor. That is, the gas/solid reaction proceeds deep in the semiconductor crystal for a lengthy exposure, and the changes deep in the crystal are slow and not reversible. Another problem, which has already been mentioned is that the reaction is slow.

OBJECTS AND SUMMARY OF THE INVENTION

An object of this invention is the provision of a solid state gas detector which has a reversible response.

Another object of this invention is the provision of a solid state gas detector which provides a more rapid response than gas detectors of its type known heretofore.

Yet another object of this invention is the provision of a new, novel and useful solid state gas detector.

The foregoing and other objects of this invention are achieved in an arrangement wherein a semiconductor substrate or support is chosen such that it will not react with the gas of interest. The surface of the support is covered with a gas sensitive additive material which is of a type which reacts reversibly and selectively with the gas of interest. This material is deposited on the support in a disperse and crystallite form, on the order of 100 angstroms in size, so that the reactions with the gas can go to equilibrium rapidly with the small crystallite. The additive material provides the surface state of the support and as a result controls the electrical properties of the support. Measurement of these electrical properties then reflects the chemical interaction between the surface state additive and the gas.

The novel features of the invention are set forth with particularity in the appended claims. The invention will best be understood from the following description, when read in conjunction with the accompanying drawings.

BRIEF DESCRIPTION OF THE PREFERRED EMBODIMENT

Figure 1:
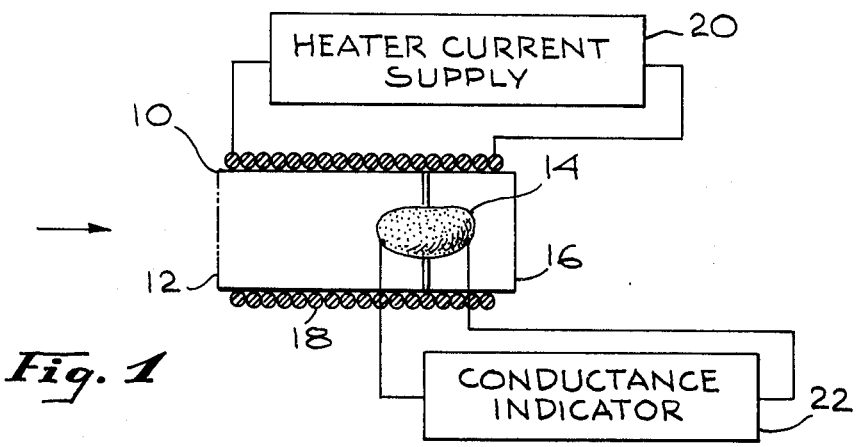
FIG. 1 is a schematic diagram of an embodiment of the invention.

The operation of the gas sensing device in accordance with this invention is based on two interactions, first a chemical interaction between the gas and the surface state of the invention (the surface state will in the following discussion also be referred to as the additive), and second, an electron exchange between the surface state additive and the semiconductor support. Thus there are three phases of interest, the gas, the additive, and the semiconductor support. The additive is a catalyst, chosen for example from the extensive catalyst literature, such that it reversibly reacts with or actively catalyzes a reaction of the gas of interest, but is chosen so that at the operating temperature it is less sensitive to other prospective ambient gases. The catalyst is highly dispersed on an outer semiconductor support, so that the gas/catalyst rapidly reaches a steady state. The semiconductor support is chosen so that at the operating temperature it is unreactive toward the ambient atmosphere but exchanges electrons with the catalyst surface state. As a gas/catalyst reaction changes the chemical properties of the surface state, these changes may be observed by measuring the electrical properties of the semiconductor support.

Another reaction which may be used, in accordance with this invention, may be termed an acid/base reaction. For example, Lewis Acids and Bases provide a surface state controlling the electrical properties of semiconductors. Still another reaction may be considered which may be termed REDOX reactions. Such reactions are acceptable since a reducing agent or oxidizing agent surface additive, if matched with an appropriate semiconductor can obviously donate or accept electrons from a semiconductor controlling its conductance. Species that form coordination complexes, e.g., with transition metal ions, can be used with the transition metal ion itself if used as a surface state or surface additive on an appropriate semiconductor. For example a system based on coordination complex formation can be appropriate for detecting carbon-monoxide.

The method of making a detector in accordance with this invention is to make a solution of the selected surface state material. The semiconductor material should be in powder form. The powder and solution are then mixed to form a heavy slurry. The slurry is then dried and pelletized. The procedure just described is the normal and well known procedure for impregnating a material with a catalyst. The word "impregnate" as used here is to be given the meaning given in the catalyst literature, which is to disperse a solid substance (the catalyst or other additive of interest) over the surface and into the pores of a support material by a technique such as described above. By way of example of a detector in accordance with this invention, Vanadium Pentozide $V_2O_5$ was deposited on the semiconductor titanium dioxide $TiO_2$. $V_2O_5$ is an excellent catalyst for the oxidation of xylene in air. After pelletizing, the incoming air and pellet were maintained at a temperature of 400° C. The presence of xylene in one atmosphere of oxygen is readily detected.

Figure 2:
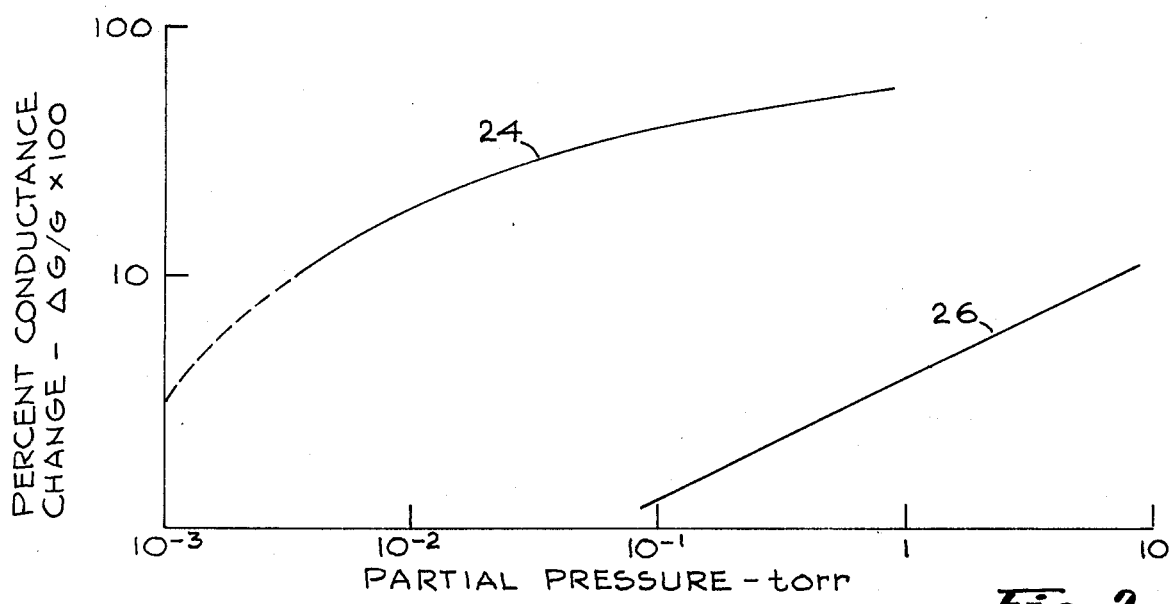
FIGS. 2 and 3 are curves illustrating responses of an embodiment of the invention to different gases.

As another illustration, in order to detect $NO_2$, for the reactant, the surface additive selected was sulfanilic acid because of its known specific reaction to the form diazo sulfanilic acid. The semiconductor support selected was nickel oxide. This was chosen because the sulfanilic acid has electron donor properties. Thus it tends to raise the electron density in n type semiconductors and lower the hole density in p type semiconductors. The p type material is preferable because the electron donor properties of sulfanilic acid would lead to a high resistance in the pressed semiconductor pellet and, thus, to relatively high sensitivity to interaction of the sulfanilic acid with an electron acceptor. Also, a p type material is particularly desireable because it reduces the problem of poisoning, i.e., in the case of n type semiconductors, one must keep the temperature of the sensor high enough to desorb atmospheric oxygen. (For example 400° C in the case $TiO_2$. The p type semiconductor chosen was lithium-doped nickel oxide) NiO:Li, sulfanilic acid was deposited on the NiO:Li powder (5% sulfanilic gas by weight) and pellets were pressed into coated material. As shown in FIG. 2, measurements indicated a satisfactory sensitivity to the presence of xylene and also to dioxide. With no sulfanilic acid deposited, the pellet is insensitive to xylene and to nitrogen dioxide.

FIG. 1 is a schematic drawing of an embodiment of this invention. It comprises a hollow container 10 with means at one end 12 for admitting a sample of the gas to be tested. A pellet 14 of a semiconductor support with a surface additive, made, as described above is supported near the other end of the container. The other end 16 of the container has openings permitting the gas sample to escape.

The container is surrounded by heating wires 18 whose function it is to maintain the temperature of the pellet at a value at which will not be poisoned by the ambient gases, and also to heat the incoming air sample. A heating current supply 20 supplies the required heating current to the resistance wires 18. A conductance indicator 22 is connected across the pellet 14. A conductance indicator may be any suitable type of indicator such as a typical ohn meter, or a warning device which turns on a light or a buzzer when the conductance exceeds a predetermined level.

FIG. 2 shows two curves, respectively 24, 26. The curve 24 represents the fractional changes in conductance of a pressed pellet of $TiO_2$ impregnated with $V_2O_5$ as a function of gas partial pressure, the gas in that instance being xylene. The curve 26 represents the results obtained when the same pressed pellet is exposed to CO. In both instances, the carrier gas was one atmosphere oxygen and the temperature of the gas was 400° C.

Figure 3:
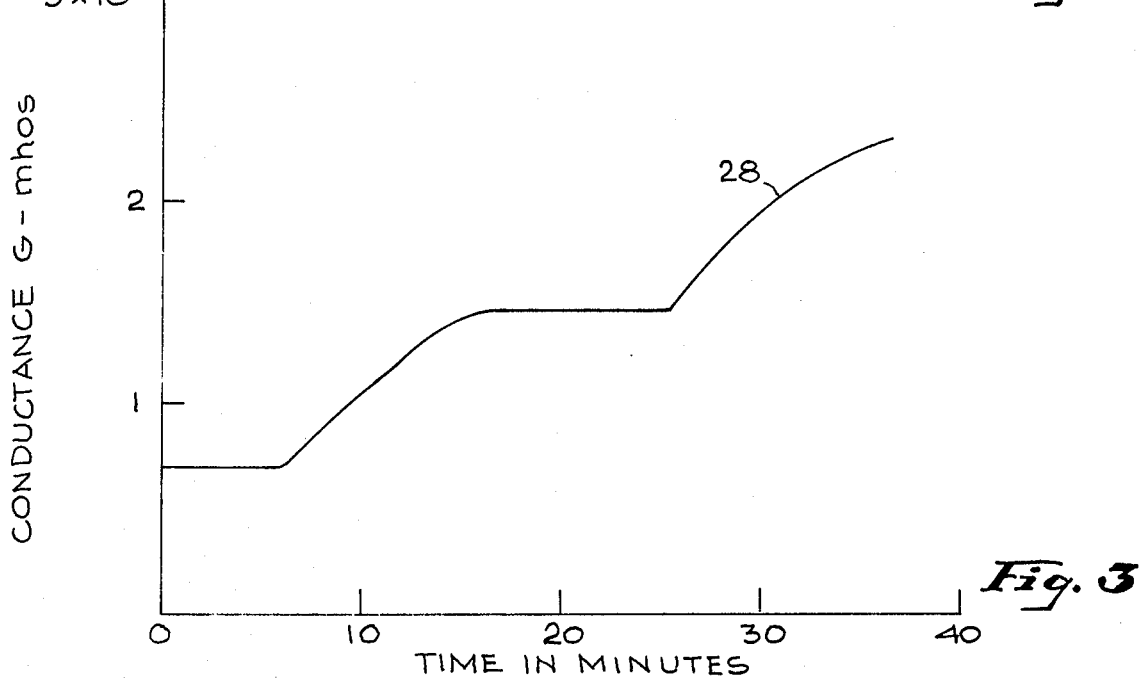

FIG. 3 shows a change in conductance obtained for a NiO-Li sulfanilic acid pellet which was exposed to $NO_2$. The carrier gas here was air and the temperature was 100° C.

From the foregoing it will be seen that there has been described and shown a novel and useful gas detector.

What is claimed:
1. A gas detector comprising:
    a semiconductor support which is substantially nonreactive to a gas to be detected,
    a surface additive means which is a catalyst deposited solely on said semiconductor support surface and in pores in said surface, for exchanging electrons with said semiconductor in the presence of said gas to be detected to change the conductivity of said semiconductor, and
    means for detecting the change in conductivity of said semiconductor support.
2. A gas detector as recited in claim 1 wherein said semiconductor support is NiO:Li and said surface additive means is sulfanilic acid.
3. A gas detector as recited in claim 1 wherein said semiconductor support is titanium dioxide and said surface additive is vanadium pentoxide.
4. Apparatus for detecting a predetermined gas comprising:
    a compressed pellet of semiconductor powder particles which are not reactive to said gas impregnated with a surface additive, which is a catalyst which is deposited solely on the surface and in pores of said powder particles, which in the presence of said gas exchanges electrons with said semiconductor powder particles, and
    means for measuring the change of conductivity of said compressed pellet.
5. Apparatus as recited in claim 4 wherein said apparatus includes
    means for heating acid compressed pellet and gas to be detected to a predetermined temperature.
6. A method of making a detector for a predetermined gas comprising:
    depositing a surface additive which is a catalyst solely over the surface and in pores of powder particles of a semiconductor material which is not reactive with said gas, which surface additive, in the presence of said gas, can exchange electrons with said semiconductor support,
    compressing said powder particles upon which said surface additive has been deposited to form a pellet, and
    connecting a conductivity measuring means to said pellet.

* * * * *